United States Patent [19]
Denckla

[11] 3,951,777
[45] Apr. 20, 1976

[54] ISOELECTRIC FOCUSING DEVICES

[75] Inventor: William Donner Denckla, Tenafly, N.J.

[73] Assignee: Hoffmann-La Roche Inc., Nutley, N.J.

[22] Filed: Apr. 24, 1975

[21] Appl. No.: 571,160

Related U.S. Application Data

[63] Continuation-in-part of Ser. No. 487,081, July 10, 1974.

[52] U.S. Cl. .......................... 204/299 R; 204/180 R
[51] Int. Cl.² .................. B01D 13/02; C25D 13/00
[58] Field of Search ............. 204/180 R, 180 G, 299

[56] References Cited
UNITED STATES PATENTS 3,355,375  11/1967  Badgley .............................. 204/299
3,616,456  10/1971  Valmet ............................... 204/299
3,718,559   2/1973  Wallace .......................... 204/180 G Primary Examiner—T. Tung
Assistant Examiner—A. C. Prescott
Attorney, Agent, or Firm—Samuel L. Welt; Jon S. Saxe; George M. Gould

[57] ABSTRACT

Ampholytes are rapidly separated with high resolution in preparative scale by isoelectric focusing at high power inputs. An improved technique for isoelectric focusing involves sequential treatment of an ampholyte mixture in successively smaller focusing units without substantial dilution. Improved isoelectric focusing devices operating at high power inputs, with highly efficient heat dissipation, are described.

19 Claims, 3 Drawing Figures

ISOELECTRIC FOCUSING DEVICES

RELATED APPLICATIONS

This case is a continuation-in-part of application Ser. No. 487,081, filed July 10, 1974.

BACKGROUND OF THE INVENTION

The separation and purification of complex molecules of biological interest has been the subject of extensive research. Since many of these molecules are ampholytes, they are theoretically amenable to separation by electrophoretic techniques. A mixture of ampholytes in solution, when subjected to a direct current electric potential will arrange within this electric potential according to isoelectric point, thereby resulting in separation.

In recent years, an improved technique for separation of ampholytes, known as isoelectric focusing, has been developed. According to this technique, an artificial pH gradient is established by use of a mixture of synthetic compounds (referred to as carrier ampholytes). Upon electrophoresis of an ampholyte mixture in such a pH gradient, which acts as buffer, the ampholytes arrange themselves within this gradient. In essence, each ampholyte molecule migrates towards the pH value in the gradient where it is isoelectric, that is, where its net charge is 0. The focusing thus takes place at the point where the pH is equal to the pI of the ampholyte.

Detailed treatment of the theory and techniques of isoelectric focusing may be found in Haglund, *Methods of Biochemical Analysis*, Vol. 19, page 1; and *Annals of the New York Academy of Sciences*, Vol. 209, "Isoelectric Focusing and Isotachophoresis".

Recently, a series of devices for use in isoelectric focusing have been described in Valmet in U.S. Pat. No. 3,616,456 and *Science Tools*, Vol. 16, page 1 (1969). These devices have a series of chambers (usually "U-tubes" or "V-tubes") disposed one after the other. The advantage of such a system is that if contamination occurs in one chamber, for example by precipitation of a solid, this does not result in contamination of the entire system. These devices were described as operating at relatively low voltages, from about 800 to 2400 volts, and with a power input of about 15 to 20 watts for a 45 ml. unit. Under these conditions, there is a limitation upon the resolution, the capacity, and, particularly, the speed of an electrophoretic separation since speed is directly proportional to the applied voltage and resolution is proportional to the square root of the voltage. The time factor becomes critical when one is dealing with sensitive ampholytes.

Thus, it would be desirable to develop techniques, and devices therefor, to allow for preparative separation of ampholytes with high resolution, at high speed, and with great reproducibility.

DETAILED DESCRIPTION OF THE INVENTION

The present invention is concerned with new improved techniques for ampholyte separation and with devices therefor.

More specifically, the present invention relates to techniques for isoelectric focusing in pH gradients, and to valuable improvements in techniques allowing for rapid, large-scale, high resolution separation of ampholytes. Another aspect of the present invention is the development of a new series of devices which are amenable for use with the improved separation techniques.

The present techniques and instrumentation allow resolution of ampholytes to the theoretical limits of currently available carrier ampholytes. Compared to known instrumentation, the present devices allow an increase of approximately 10-fold in electric field strength per unit distance, and 30-fold in total applied electric potential; 3-fold in resolving power; 6-fold in power dissipation per unit volume, and up to 300-fold total power dissipation; 8-fold in speed; and 500-fold in weight of ampholyte material which can be separated. Thus, the present devices may be used at voltages up to 100 kv and can dissipate efficiently 6000 watts or more.

In one aspect of the present invention, there is an improved technique for isoelectric focusing of ampholytes which comprises conducting the focusing under conditions which allow for a large power input relative to the volume of the ampholyte solution, while keeping the temperature of the solution relatively constant.

In prior art instruments such as those of Valment hereinabove mentioned, there is a significant increase in temperature of the ampholyte solution, even when utilizing a relatively low input relative to the solution volume. Thus, in a typical instrument, there was reported to be approximately an average 7°C rise in solution temperature under conditions of half a watt power input per milliliter of solution.

The present technique, and the instruments therefor, allow for a considerably higher power input, of at least 3 watts per milliliter of solution, resulting in an average 7°C rise in solution temperature.

As mentioned above, it is critical to keep the temperature of the ampholyte solution relatively constant. Many of the ampholytes of biological importance are proteinaceous in nature and they are highly susceptible to denaturization by heat. As a rule, most isoelectric focusing of such materials is carried out at reduced temperatures, for example, about 0° to 5°C, to avoid such denaturization of other harmful effects. A significant rise in temperature above this range can, in many cases, destroy the valuable biological activity or specificity of the molecules attempted to be purified.

In the prior art, as demonstrated by the devices of Valmet, such attempts to keep temperature increases to a minimum (which were not very effective) had to be accomplished by sacrificing the power input that could be used.

It is well known (see, for example, Svensson, *Acta. Chemica. Scandinavica*, 15, 425 (1961)) that the resolving power of an isoelectric focusing system is directly related to the square root of the potential (voltage) applied to the system. While the resolving power is technically independent of the current, the time necessary for resolution (that is, to achieve an approximate equlibrium condition) is a function of the power input, that is, the wattage. The use of a low wattage instrument results in a lengthy period of time, e.g., 2 weeks, in order for isoelectric focusing to occur. Because of the instability of many of the ampholytes, such manipulation for an extended period of time, particularly if temperatures are not kept relatively low, is not desirable.

The present technique of utilizing a high wattage input without significant rise in solution temperature allows for isoelectric focusing with even higher resolution, and in much shorter periods of time, for example, about 1.5 hours, for an instrument of comparable volume.

In another aspect of the present invention, a highly improved isoelectric focusing result may be obtained by sequential isoelectric focusing using a series of devices of successively smaller volume, without substantial dilution of the ampholyte solution.

In the prior art technique, as particularized by Valmet, the number of chambers in a particular isoelectric focusing unit was determinative of the resolution. Thus, the resolving power has been defined as the number of pH units in the pH gradient divided by half the number of chambers in the unit. For a pH gradient of 7 pH units and a unit with 30 chambers, the resolving power would be 0.47 pH units. To achieve a resolving power of 0.01 pH units with the same pH gradient (7 units), there would be required a cell with greater than 1000 chambers.

By means of the present technique, resolutions as low as 0.01 pH units (theoretical limit of presently available carrier ampholytes) may be achieved, starting with a pH gradient of 7 pH units, by utilizing three successively smaller units having 10 compartments each, for a total of 30 compartments. The key feature of the present method is the use of the series of successively smaller devices without substantial dilution of the ampholyte solution.

In a preferred method, each of the series of devices has the same number of chambers, and the ratio of the volume of each unit to the next smaller unit is approximately equal to the number of chambers in each unit.

Thus, for example, three typical units, having 10 chambers each, of volume 2100 ml, 215 ml and 25 ml, respectively, may be utilized. The crude ampholyte mixture is placed in the 2100 ml device with a carrier ampholyte establishing an artificial pH gradient of from pH 3 to pH 10 (7 pH units), and subjected to isoelectric focusing. The one chamber (210 ml) containing the desired material is determined and its contents are transferred to the next smaller device (215 ml). Only minimal dilution is required to effect a quantitative transfer. The pH gradient in this device should be approximately 0.7 pH units. The isoelectric focusing is repeated and the chamber (approx. 22 ml volume) containing the desired material (pH gradient approx. 0.07 pH units) is again determined. After transfer to the next smallest device (25 ml) the focusing is repeated. After focusing, the chamber (approx. 2.5 ml) containing the desired material is determined and the product, now present in a pH gradient of approximately 0.01 pH units, is isolated by conventional techniques.

By utilizing the present methodology with devices allowing for increased power input as described above, each of the isoelectric focusing steps may be carried out in a relatively short period of time. Furthermore, the use of a total of 30 chambers can produce a result which was heretofore only theoretically possible utilizing a device having at least 1,000 chambers.

Even larger devices, of about 20 liter volume, may be used to give a crude separation of large amounts of material, which may then be further purified on successively smaller units as described above.

The present method also offers a tremendous advantage over a dilution technique whereby the contents of a single chamber after isoelectric focusing are diluted and refocused in a device of the same size. Dilution of the ampholyte solution results in a loss of the buffering capacity of the carrier ampholytes so that the resolution attainable is diminished.

The process of improved isoelectric focusing by effecting a large power input while keeping a relatively constant temperature of the ampholyte solution is achieved by the use of a new series of isoelectric focusing devices. A key feature of such devices is the efficient dissipation of heat generated by the large power input, by means of an improved cooling system. This efficient cooling system is made possible by careful selection of materials, by careful disposition of the cooling elements and by structural considerations allowing for stability in the presence of high voltages, simple and economical construction, and built-in safety features.

The improved electrophoresis devices for isoelectric focusing are characterized by being comprised of a substantially rectangular, box-shaped receptacle for receiving a solution of an ampholyte mixture to be separated, said receptacle having a bottom, two opposite end walls, two opposite front and rear walls, two electrodes inserted in said receptacle proximate to said opposite end walls and adapted to be connected to a direct voltage source, said receptacle being provided with a plurality of impermeable walls, said impermeable walls extending parallel to said end walls and being disposed so that first alternate walls extend to the receptacle bottom and remaining alternate walls extend proximate to the receptacle bottom so as to divide the receptacle into a plurality of continuously communicating U-tube chambers. The improvements provided by the present device comprise:

a. providing a minimal absolute thickness of the water film in the arms of the U-tube chambers by controlling the distance between the walls of the U-tube chamber to about 1 mm for units having volumes up to 200 ml., 1.5 mm for volumes up to 2,000 ml. and 3.0 mm for volumes up to 20 l.;

b. providing a ratio between the height of the U-tube arms to the inter-wall distance of the arms of the U-tube of greater than 50 to 1 and preferably about 100 to 1, said ratio being increased even further if the distance in (a) is increased beyond the levels indicated;

c. providing a ratio between the width of each of the U-tube arms to the absolute length of the total flow path between the electrodes of less than 1 to 15;

d. providing an electric field that is symmetrical along the entire length of the electrode by utilizing a metal foil or wire grid electrode having an area that exceeds 10 times the cross-sectional area of the area defined by the inter-wall distance in the chamber and the width or depth of the chamber;

e. cooling means associated with said impermeable walls for causing highly efficient heat removal from the ampholyte solution which is proximate to said impermeable walls;

f. high voltage electrical insulation at all surfaces of the receptacle which contact the ampholyte solution during normal use; and g. water- and high voltage-resistant sealing means for providing leak-proof seals at all internal joints of said receptacle which contact the ampholyte solution during normal use.

One of the major problems associated with iso-electric focusing, particularly when operating at high voltages, arises from the phenomenon of electro-osmotic flow. This large volume flow of water from one electrode to the other will cause the ampholytes being separated to migrate from their true iso-electric points. When the ampholyte has a relatively weak charge density such migration can be quite extensive until the charge on the ampholyte provides an electrostatic force sufficient to offset the force of the osmotic flow. In addition, the osmotic flow will occur mainly in the center of the channel and will fall off rapidly towards the sides. This will cause the concentration gradient to be bullet shaped and thus will not be normal to the long axis as desired for maximum resolution. Obviously, the above factors reduce substantially the ability of the iso-electric focusing apparatus to function effectively as an analytical or preparative device.

It has now been discovered that the effects of electro-osmotic flow can be minimized to the point where iso-electric focusing devices can be constructed which operate near the theoretical limits of time, efficiency, resolution and accuracy. Such minimization is obtained by constructing such devices in accordance with several critical dimensional parameters.

The first critical dimension which must be incorporated into the instant iso-electric apparatus is to provide a water film of minimum thickness in the U-tube arms. This is conveniently accomplished by employing a critical distance between the walls of the U-tube. Such distance is about 1 mm for an apparatus of up to 200 ml., 1.5 mm for an apparatus of up to 2,000 ml. and 3.0 mm for an apparatus of up to about 20 l.

A second critical dimension involves the ratio of the height of the U-tube arms to the thickness of the water film. Such ratio must exceed 50 to 1 and most peferably should be about 100 to 1. Should the value of the thickness of the water film be increased beyond the values indicated above it is necessary to increase the height to thickness ratio. Obviously there is not much practical leeway in this adjustment as the height must increase logarithmically with any increase in the thickness.

Another critical dimensional parameter which must be observed is the ratio of the width of the U-tube arm to the absolute length of the flow path between the electrodes. Such ratio must be less than 1 to 15. In this manner one is specifically able to overcome the bulleting effect of the electro-osmotic flow on the ampholyte concentration gradient. Thus the resolution of the device will be improved in that there will be less chance of a separated ampholyte being found in more than one chamber.

The electrode configuration in the instant device is also an important factor in successful operations, particularly when high voltages are to be employed. In order to achieve an electric field which is symmetrical along the entire length of the electrode it is necessary to utilize an electrode having an area that is at least 10 times the cross-sectional area of the area defined by the inter-wall distance in the chamber the water film in a U-tube chamber. This is most conveniently accomplished by using a metal foil or a wire grid, preferably a platinum foil or grid, as the electrodes.

When all of the above parameters are adhered to in the construction of the iso-electric device it will be found that such device will operate at near theoretical conditions. Desired ampholytes will be separated rapidly and efficiently, they will be found at or near their true iso-electric points, peak to peak discrimination between separated ampholytes will be maximal and peak to height ratios for each ampholyte will be maximal.

Another improvement in design and operation serving to enhance the efficiency of the devices of the present invention relates to preventing carbon dioxide absorption in the water during the separation process. This can be accomplished by providing a leak-proof receptacle enclosing the entire device which would prevent access to the ambient atmosphere and/or providing a carbon dioxide free atmosphere within the device by introducing a stream of air scrubbed free of carbon dioxide, i.e., by passing through a caustic solution. Elimination of carbon dioxide absorption during operation helps prevent a drift in the pH gradient.

Another of the improvements in the present device is cooling means associated with the impermeable walls for causing highly efficient heat removal from the ampholyte solution which is proximate to said walls. In preferred embodiments, the cooling means includes means for passing coolant through channels in the impermeable walls extending from the front to the rear of the device.

There are three major components involved in the highly efficient heat removal. The first is the creation of turbulence at the boundry layer between coolant and the impermeable walls. The second factor is heat transfer (conduction) through the impermeable walls. The third factor is convection effects caused by a not perfectly uniform temperature of the ampholyte solution.

The boundary layer turbulence is caused by a shear effect of the coolant on the impermeable wall inside surfaces due to the coolant passing at high velocity through a narrow channel within the impermeable wall. The average velocity of coolant through the impermeable walls should be at least 1 ft/sec, and the width of the coolant channel should be between about 1 and 3 mm in order to cause the boundary layer turbulence.

Factors affecting the conduction and convection effects on the ampholyte solution include the thickness of the impermeable walls between the coolant and the ampholyte solution and the distance between adjacent impermeable walls. In order to create the desired effect, the thickness of the impermeable wall between the coolant and the ampholyte solution should not exceed 3 mm and is preferably between about 0.8 and 2.5 mm. The impermeable walls are pre-determinedly spaced, in relation to the receptacle size, so as to maximize convection and conduction effects by providing high surface area contact with the ampholyte solution.

Other factors having a more general effect on the rate of heat removal from the ampholyte solution are: nature of coolant, temperature of coolant, thermal conductivity of the impermeable walls, ampholyte solution, and coolant; viscosity of coolant and ampholyte solution; and so forth. One will normally control the temperature of the coolant, in conjunction with other parameters such as flow rate, in order to optimize heat dissipation, depending upon the nature and stability of the ampholyte being separated. A temperature range of from about $-60°$ to about $+50°C$. may be mentioned, with a preferred temperature range for most denaturable ampholytes of from about $-10°$ to about $+10°C$.

A variety of conventional coolants may be utilized. Among these coolants are liquid coolants such as water, mixtures of water with various organic solvents to allow for cooling without freezing below the normal freezing point of water, for example, ethylene glycol, isopropanol, and the like; fluorocarbon coolants; cooled gases such as air; and the like.

The coolant is allowed to travel through the channels in the impermeable walls, preferably by pumping means, adjusted so as to create the desired velocity as described above. In a suitable arrangement, coolant is introduced by appropriate means into a chamber, or plenum, either at the front or rear of the device, from which it is fed into the plurality of impermeable walls, exiting therefrom into another plenum from which the coolant is removed from the device. Preferably, a closed coolant is utilized whereby expended coolant removed from the device is passed through external heat exchanging means to reduce the coolant temperature for recirculation back into the isoelectric focusing device.

In the following, the operation and advantages, as well as additional characteristic features of devices for isoelectric separation, according to the invention, will be further described with reference to the accompanying drawings which show, by way of example, a number of different embodiments of the invention. In the drawings.

Figure 1:
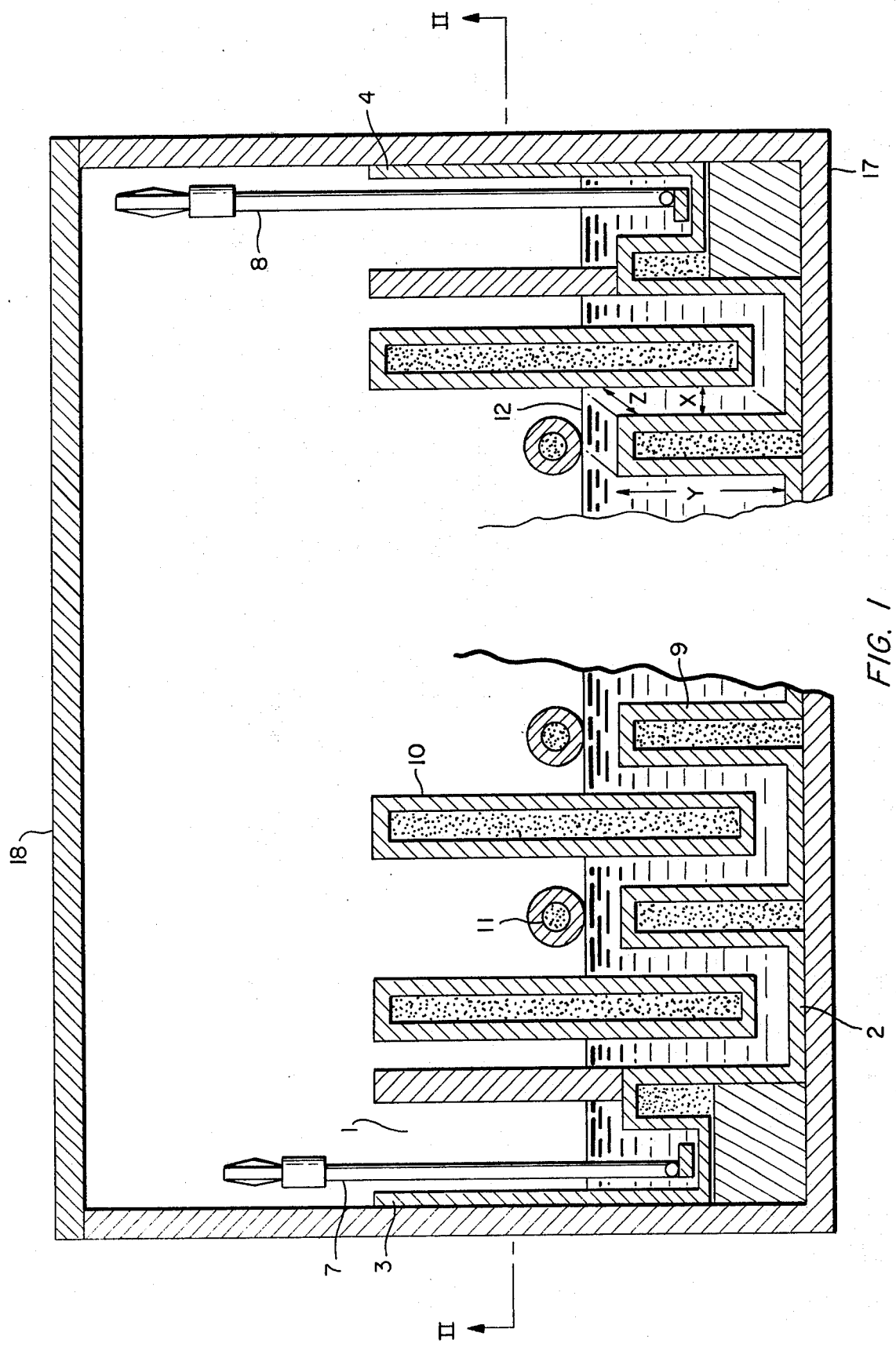
FIG. 1 shows schematically a first embodiment of a separation device according to the invention in a front cross-section.
Figure 2:
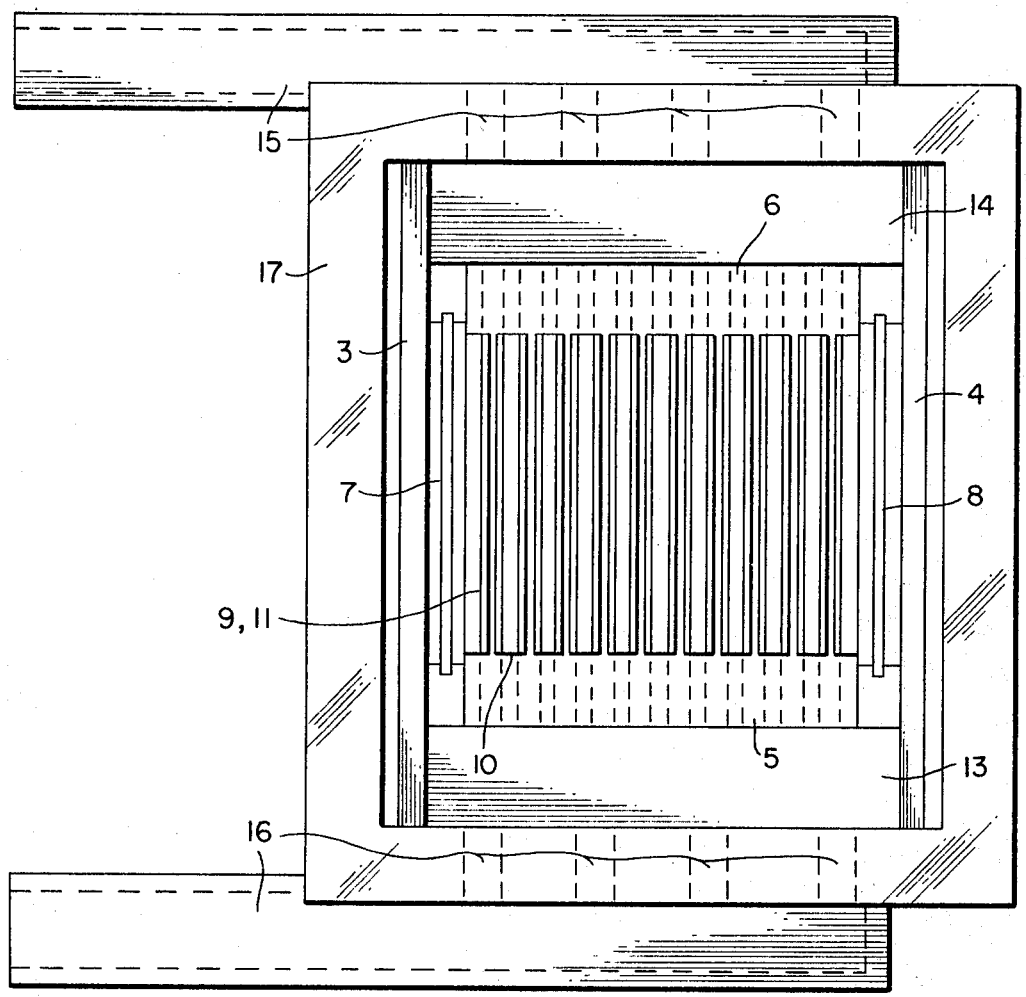
FIG. 2 is a top view of the device in FIG. 1 taken along the line II—II in FIG. 1, with the top cover removed.
Figure 3:
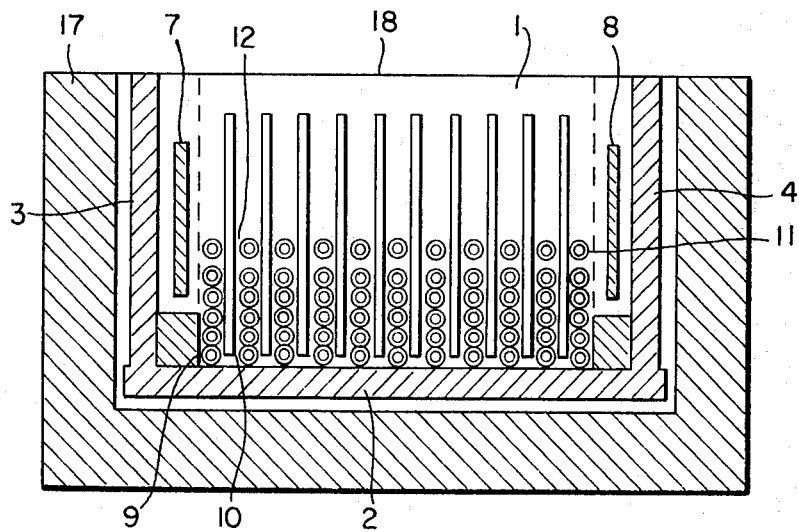
FIG. 3 shows schematically a second embodiment of a separation device according to the invention in front cross-section.

The isoelectric focusing device according to the invention, illustrated in FIGS. 1, 2 and 3, comprises a substantially rectangular, box-shaped receptacle 1 for receiving a solution of an ampholyte mixture to be separated. This receptacle has a bottom 2, two opposite end walls 3, 4 and two opposite front and rear walls 5, 6. Two electrodes 7, 8 are inserted in the receptacle proximate to the opposite end walls and are adapted to be connected to a direct voltage source. The electrode is a metal foil or wire grid, preferably platinum, when has an area greater than 10 times the cross-sectional area of the water film ($x \cdot z$). Particularly preferred electrodes are platinum foils secured to glass supports. The device is provided with a plurality of impermeable walls 9, 10. These impermeable walls extend parallel to the end walls and are disposed so that first alternate walls 9 extend to the receptacle bottom, and remaining alternate walls 10 extend proximate to the receptacle bottom, preferably between about 1 and 10 mm therefrom. The disposition of the impermeable walls results in the receptacle being divided into a plurality of continuously communicating U-tube chambers.

The number of U-tube chambers in any one device may vary from 3 to as high as 100, but preferred embodiments have approximately 10 U-tube chambers.

In preferred embodiments, the impermeable walls are essentially hollow, having a channel for the passage of coolant therethrough. In one embodiment of the present device, as illustrated in FIGS. 1 and 2, the impermeable walls are pictured as substantially rectangular in shape, having a rectangular channel for coolant. In FIG. 3, another embodiment is pictured having first impermeable walls 9 constructed of a series of vertically contiguous tubes for passage of coolant. In still another embodiment, all impermeable walls 9 and 10 are constructed of such vertically contiguous tubes.

Preferred embodiments of the present device further include additional cooling means 11 arranged above first alternate walls 9 so as to be in contact with the surface 12 of the ampholyte solution during normal use. In such a manner, effective cooling of ampholyte solution surface 12, at the point which would normally be minimally cooled by the other cooling means, is provided. Such cooling means 11 is normally constructed of similar material as impermeable walls 9 and 10. The shape of such means is not critical, although a substantially circularly-shaped tube is preferred.

The critical dimension parameters are indicated in FIG. 1. Thus the inter wall distance dimension is shown as $x$, the U-tube arm height is $y$ and the width or depth of the U-tube arm is $z$.

As shown in FIG. 2, coolant is introduced into the device through a plenum 13, passing from there through the plurality of impermeable walls 9, 10 and, if desired, through additional cooling means 11, and exiting through a plenum 14. Means 15 and 16, for introducing and removing coolant, communicating with plenums 13 and 14, are also provided. As mentioned above, various liquid and gaseous coolants may be used. Liquid fluorocarbons are particularly preferred for their property of being electrically non-conductive, so that the danger of an electrical short between the (aqueous) ampholyte solution and the cooling means caused by accidental breakage, leakage or otherwise, at the high operating voltages of the devices, would be significantly reduced.

Another feature of the present devices is that high voltage electical insulation is provided at all surfaces of the receptacle which contact the ampholyte solution during normal use. This high voltage electrical insulation should have a dielectric strength of at least 500 volts/0.001 inch. A preferred insulation is glass. Since the devices operate at potentials above ground of up to 100,000 volts the need for electrically non-conducting inner surfaces which will insulate against and be stable to the high voltages employed without shorting, is extremely critical and readily apparent.

If a material such as glass is used for insulation, it is normally of sufficient rigidity and strength to serve both as support for the structural members, as well as insulating means. If desired, suitable insulating materials may be used to coat otherwise non-insulating materials. For example, one may coat rigid materials such as metals with, for example, glass. For ease of construction, as well as economy, it is preferred that the same material be used both for support and insulation purposes, preferably a material such as glass.

A third feature of the present device is the use of water- and high voltage-resistant sealing means for providing leak-proof seals at all internal joints of the receptacle which contact the ampholyte solution during normal use. The need for such leak-proof seals is readily apparent in view of the hazards attendant to the use of instruments involving such high voltages. If a leak were to occur between the chamber containing ampholyte solution and, for example, aqueous cooling means, there would be created an extreme danger to the operator. The sealing means should be stable to the aqueous ampholyte solutions and be able to withstand, for extended time periods, the high voltages employed. Preferred sealing means include silicone-base sealers.

The receptacle 1 is preferably surrounded by an outer electrically non-conductive shield 17, and covered by an electrically non-conductive cover 18. The cover is preferably removable, allowing for sampling, etc., from the open U-tube chambers during operation, a decided advantage over previous devices. Suitable gaskets and seals may be introduced into the cover to insure insoluation from the ambient atmosphere as a means of excluding carbon dioxide or a suitable tube can be inserted through the cover in a manner known per se to serve as the means for introducing carbon dioxide free air.

The devices of the present invention may be constructed in various sizes, for example, from about a volume (total volume of ampholyte solution) of about 1 ml. to a volume of, for example, 100 liters. As explained above, a series of devices of decreasing volume may be used sequentially to purify ampholyte mixtures in preparative scale.

It is preferable to utilize the present instruments in conjunction with the above-described methodology, whereby improved ampholyte separations are achieved by performing the isoelectric fractionations at a power input of up to 3 watts per milliliter of ampholyte solution with a resultant average temperature increase of no more than 7°C. When a series of such devices is additionally utilized in a sequential fashion, extremely rapid, high resolution separations of gram quantity samples of ampholyte mixtures — heretofore unachievable in the art — may be performed.

Among the types of ampholytes which may be separated utilizing the present devices and methodology, are proteins, particularly those of pharmaceutical interest.

More specifically, any ampholyte which is soluble or recoverable at its isoelectric point without irreversible denaturation may be separated. Among these ampholytes are enzymes, hormones, cell particles, viruses, structural proteins, blood proteins, cerebrospinal fluid proteins, urine proteins, and the like.

As mentioned above, the technique of isoelectric focusing utilizes an artificially created pH gradient which is established by a mixture of synthetic compounds referred to as carrier ampholytes. These carrier ampholytes are generally of low molecular weight, and after the desired separation of the sample compounds is achieved, the desired materials are separated from the carrier ampholytes by standard chemical and physical techniques such as, for example, dialysis or chromatography.

The use of the present devices and techniques for the purification of a typical ampholyte mixture is described below:

EXAMPLE 1

This example demonstrates the speed of separation of ampholyte mixtures utilizing the devices of the present invention:

The device used had a 25 ml capacity and contained 10 U-tube chambers. The receptacle itself was constructed entirely of glass with all joints being sealed with Dow-Corning No. 734 adhesive. The unit was constructed essentially as depicted in FIGS. 1 and 2. The distances between adjacent walls of the U-tubes, thickness of the glass walls between the coolant and the ampholyte solution, and the width of the cooling channels within the walls, were all 1 millimeter. The coolant utilized was a liquid fluorocarbon which entered the device at a temperature of 2°C. The velocity of the coolant through each wall of the device was approximately 2 feet per second.

20 mg of whole blood was dissolved in 25 ml water containing 1% Ampholines (LKB), pH 3.5–10. The device was operated at a voltage of from 3,000 to 7,000 volts with an average power input of 75 watts. After 1.5 hours, 90% of the hemoglobin (as determined by optical density measurement) was focused in one of the 10 chambers of the device.

EXAMPLE 2

This example demonstrates the high resolution that can be obtained using successively smaller isoelectric focusing units in sequence without substantial dilution of the ampholyte mixture:

200 mg of the $100,000 \times g$ supernatant of an aqueous extract of rat olfactory bulbs was subjected to isoelectric focusing. This material was dialyzed and dissolved in 2 liters of 0.8% Ampholines (LKB), pH 3–6, and placed in a device substantially identical in design with that described in the previous example, except that additional cooling means 11 were not present. This device had a capacity of approximately 2 liters and contained 10 chambers. After reaching equilibrium on this device, the 200 ml U-tube which contained most of the olfactory protein was then placed, after appropriate dilution with 20 ml of distilled water, in a 220 ml unit of identical design. After equilibrium was reached on this unit, the tube containing the maximum immunoreactive protein was then placed in a 25 ml unit, after appropriate dilution with 3 ml distilled water. After equlibrium was reached on this third instrument, the distribution of the desired protein was determined by immunoassay and discontinuous gel electrophoresis. The majority (90%) of the activity was concentrated into 5 tubes on this instrument in a final volume of 11 ml, compared with the starting volume of 2000 ml. This represents an approximately 50-fold purification. The olfactory protein had an approximately Gaussian distribution in the 5 tubes with a standard deviation of ± 0.01–0.015 pH units. The protein was then purified on a DEAE column after removal of the Ampholines by dialysis.

I claim:

1. In an improved device for isoelectric focusing of ampholyte mixtures said device comprising a substantially rectangular, box-shaped receptacle (1) for receiving a solution of an ampholyte mixture to be separated, said receptacle having a bottom (2), two opposite end walls (3, 4), two opposite front and rear walls (5, 6), two electrodes (7, 8) inserted in said receptacle proximate to said opposite end walls and adapted to be connected to a direct voltage source, said receptacle being provided with a plurality of impermeable walls (9, 10), said impermeable walls extending parallel to said end walls and being disposed so that first alternate walls (9) extend to the receptacle bottom and remaining alternate walls (10) extend proximate to the receptacle bottom so as to divide the receptacle into a plurality of continuously communicating U-tube chambers, the improvements which comprise a. providing a distance between the walls of the U-tube chamber ($x$) of about 1 mm for devices of volumes of up to 200 ml, 1.5 mm for volumes of up to 2,000 ml. and 3.0 mm for volumes of up to 20;

b. providing a ratio between the height of the U-tube arms ($y$) to the inter-wall distance of the U-tube chamber ($x$) of greater than 50 to 1;

c. providing a ratio between the width of each of the U-tube arms to the abosolute length of the total flow path between the electrodes of less than 1 to 15;

d. cooling means associated with said impermeable walls for causing highly efficient heat removal from the ampholyte solution proximate to said impermeable walls;

e. high voltage electrical insulation at all surfaces of the receptacle which contact the ampholyte solution during normal use; and, f. water- and high voltage-resistant sealing means for providing leak-proof seals at all internal joints of said receptacle which contact the ampholyte solution during normal use.

2. The device of claim 1 wherein said electrodes comprise electrode means for producing a symmetrical electric field along the entire length of said electrode means.

3. The device of claim 2 wherein said electrode means comprises a metal foil or wire grid having an area greater than 10 times the cross-sectional area defined by the inter-wall distance of the U-tube chamber and the width or depth of the chamber ($x \cdot z$).

4. The device of claim 1 wherein said electrode means comprise a platinum foil secured to a glass support.

5. The device of claim 1 wherein the ratio between the height of the U-tube arms ($y$) to the inter-wall distance of the U-tube chamber ($x$) is about 100 to 1.

6. The device of claim 1 wherein said receptacle is arranged and constructed to prevent absorption of carbon dioxide from the ambient atmosphere during operation.

7. The device of claim 6 wherein said receptacle includes means for passing a carbon dioxide free air stream into the device.

8. The device of claim 1 wherein said cooling means includes means for passing coolant through a channel in the impermeable walls (9, 10).

9. The device of claim 8 wherein said coolant travels through said channel at an average velocity of at least 1 ft/sec.

10. The device of claim 8 wherein the coolant is liquid fluorocarbon.

11. The device of claim 8 wherein the coolant passes through the impermeable walls in a channel having a width of from 1 to 3 mm.

12. The device of claim 8 wherein the thickness of the walls between coolant and ampholyte solution is less than 3 mm.

13. The device of claim 8 wherein said impermeable walls (9, 10) are substantially hollow so as to allow the passage of coolant therethrough.

14. The device of claim 8 wherein said impermeable walls (9, 10) are comprised of a series of vertically contiguous tubes for passage of coolant therethrough.

15. The device of claim 1 wherein said impermeable walls are predeterminedly spaced in relation to the receptacle size so as to maximize convection effects in the ampholyte solution.

16. The device of claim 1 further including additional cooling means (11) arranged above first alternate walls (9) to be in contact with the surface (12) of the ampholyte solution during normal use, for providing effective cooling of ampholyte solution surface.

17. The device of claim 1 wherein said high voltage electrical insulation has a dielectric strength of at least 500 volts/0.001 inch.

18. The device of claim 17 wherein said insulation is glass.

19. The device of claim 1 wherein said water- and high voltage-resistant sealing means has a silicon base.

* * * * *